(12) United States Patent
Wang et al.

(10) Patent No.: US 9,040,017 B2
(45) Date of Patent: May 26, 2015

(54) LIVER-RECEPTOR IMAGING INJECTION, DISPENSING METHOD AND PHARMACEUTICAL COMPOSITION THEREOF

(75) Inventors: Mei-Hui Wang, Taoyuan County (TW); Wuu-Jyh Lin, Taoyuan County (TW); Hung-Man Yu, Taoyuan County (TW); Chuan-Yi Chien, Taoyuan County (TW); Ping-Yen Wang, Taoyuan County (TW)

(73) Assignee: INSTITUTE OF NUCLEAR ENERGY RESEARCH ATOMIC ENERGY COUNCIL, EXECUTIVE YUAN, Taoyuan County (TW)

( * ) Notice: Subject to any disclaimer, the term of this patent is extended or adjusted under 35 U.S.C. 154(b) by 408 days.

(21) Appl. No.: 13/243,225

(22) Filed: Sep. 23, 2011

(65) Prior Publication Data

US 2012/0107236 A1    May 3, 2012

(30) Foreign Application Priority Data

Oct. 29, 2010    (TW) .............................. 99137267 A

(51) Int. Cl.
*A61K 51/04*    (2006.01)
*A61K 51/06*    (2006.01)

(52) U.S. Cl.
CPC ......... *A61K 51/0491* (2013.01); *A61K 51/0406* (2013.01); *A61K 51/0497* (2013.01); *A61K 51/065* (2013.01)

(58) Field of Classification Search
None
See application file for complete search history.

(56) References Cited

PUBLICATIONS

Merwin et al. Targeted delivery of DNA using Yee(GalNAcAH)3, a synthetic glycopeptide ligand for the asialoglycoprotein receptor. 1994 Bioconjug. Chem. 5: 612-620.*
Yu et al. Labelling of peptide derivative with In-111 for receptor imaging. 2010 J. Label. Compd. Radiopharm. 53: 417-419. Published online Jun. 2, 2010.*
Sang Kil Ha-Kawa and Yoshimasa Tanaka, "A Quantitative Model of Technetium-99m-DTPA-Galactosyl-HSA for the Assessment of Hepatic Blood Flow and Hepatic Binding Receptor", vol. 32, Dec. 1991, The Journal of Nuclear Medicine, p. 2233-2240.
Lee et al., "Binding of Synthetic Oligosaccharides to the Hepatic Gal/GalNAc Lectin", vol. 258, Jan. 10, 1983, The Journal of Biological Chemistry, p. 199-202.
Toyama et al., "Evaluation of asialoglycoprotein receptor imaging agent as a marker of hepatic ischemia-reperfusion injury and recovery", vol. 13, 1999, Annals of Nuclear Medicine, p. 155-160.
Lee et al., "Facile Synthesis of a High-Affinity Ligand for Mammalian Hepatic Lectin Containing Three Terminal N-Acetylgalactosamine Residues", vol. 8, 1997, Bioconlugate Chem., p. 762-765.

* cited by examiner

*Primary Examiner* — Michael G Hartley
*Assistant Examiner* — Jennifer Lamberski
(74) *Attorney, Agent, or Firm* — WPAT, PC; Justin King

(57) ABSTRACT

The present invention is related to a pharmaceutical composition for a liver-receptor imaging injection, the pharmaceutical composition including a bi-functional compound which has a ASGPR specificity, wherein the bi-functional compound includes a backbone of alpha-amino acid (or the derivatives thereof) and a poly-galactosamine chain (or a poly-lactose chain) connected to the alpha-amino acid. Thereby, the pharmaceutical composition can quantify potential of liver storage ability and evaluate severity of the course of liver disease. A liver-receptor imaging injection using the same and the one-step dispensing method thereof are also provided to improve defects of iodine-labeled and overcome disadvantages of the reduced labeling-yield and the instability after autoclave sterilization.

11 Claims, 9 Drawing Sheets

LIVER-RECEPTOR IMAGING INJECTION, DISPENSING METHOD AND PHARMACEUTICAL COMPOSITION THEREOF

RELATED APPLICATIONS

This application claims priority to Taiwan Application Serial Number 099137267, filed on Oct. 29, 2010, which is herein incorporated by reference.

FIELD OF THE INVENTION

This disclosure in general relates to a pharmaceutical composition for a liver-receptor imaging injection, the use and the dispensing method thereof. More particularly, this disclosure is related to a lyophilized vial and the preparing method thereof, which dispense the liver-receptor imaging injection in one-step to improve disadvantages of labeled radiopharmaceuticals for the reduced labeling-yield and the instability after autoclave sterilization.

BACKGROUND ART

Asialoglycoprotein receptor (ASGPR) is an endocytotic cell surface receptor only expressed by mammal hepatocytes, specifically recognizing the saccharide chain with terminal galactose residues or terminal N-Acetylgalactosamine (GaINAc) residues. SPECT image of liver ASGPR is obviously better than other imaging methods and has a higher affinity and a rapid absorption for liver. When hepatopathy, the amount of ASGPR may change. According to such a property, glycopeptides or glycoproteins having galactose or GaINAc residues can be developed as liver-receptor imaging agents.

Applicability of liver-receptor imaging agents is as follows:

1. Patents suffering the liver transplantation usually have transient anoxia. Whether liver transplanting surgery succeeds will be immediately known by liver-receptor imaging after transplanting the liver.
2. Liver-receptor imaging is evidence for the real liver function. After Glycopeptides or glycoproteins having galactose residues or GaINAc residues bind to ASGPR, they may enter into liver cells by receptor-mediated endocytosis. When hepatopathy, liver cells may reduce and imaging value may lower. Therefore, the amount of the real liver function may be evaluated.

These liver-receptor imaging agents have potential for quantifying liver storage ability, and thus imaging absorption of these liver-receptor imaging agents can use to evaluate severity for the course of liver disease.

Indium-111 (In-111 or 111In) has some advantages for commonly applying in nuclear medicine, including:

(1) A suitable physical half-life (about 67 hours), and thus there being enough tome for observing the metabolic change of radiopharmaceuticals in human bodies.

(2) A very short biological half-life.

(3) A common nuclide of hospitals for easy access. Most In-111 radiopharmaceuticals, which can add In-111 in anytime to dispense for labeling, is convenient to healthcare centers and users, and thereby improve flexibility and supply reliability for usage of In-111 radiopharmaceuticals in the nuclear medicine department.

(4) Gamma-ray released from In-111 have suitable energy of about 171 key and can apply to all gamma-imaging equipment.

(5) In-111 production of Taiwanese research institute ((The Institute of Nuclear Energy Research (INER)) have been for several years, and have a well and stable quality. Thus, the said In-111 can offer hospitals and research institutions in a cheaper price to produce In-111 radiopharmaceuticals and have competitive advantages in the market.

Traditional Tc-99m-DTPA-Galactosyl-Albumin (Tc-99m DTPA-GSA) is known as a liver-receptor imaging injection which Albumin was as a backbone to connect unanticipated amount of galactosamine and diethylene triamine pentaacetic acid (DTPA). It fails to control this process to ensure that the mount of connected DTPA per batch is the same, so there will be a great difference in radiochemical specific activity of labeled Tc-99m per batch. To ensure constant radiochemical specific activity and remain imaging quality of high reproducibility, it is necessary to develop a new backbone for connecting a fixed amount of galactosamine and DTPA.

Tyrosine-glutamic acid-glutamic acid (YEE), tyrosine-Aspartic acid-Aspartic acid (YDD) and tyrosine-glutamic acid-glutamic acid-glutamic acid (YEEE) use peptides such as glutamyl-glutamic acid (EE) aspartyl-aspartic acid (DD) to be a backbone for preparing poly-saccharide chains. YEE and YDD can connect fixed amount of galactosamine and DTPA and be suitable for iodine-labeling, but their development in pharmaceutical industry are limited due to their complicated synthetic steps and low solubility. Further, oxidants such as chloramine T, iodobead, Iodogen or the like should be added when iodine-labeling. If they are used as in vivo image, purification for removing oxidants after the said steps finish is required because these oxidants are toxic for human bodies.

Imaging injections for human should conform to the criteria for labeled products which are germless and have no pyrogen. Autoclave sterilization is the most common method for sterilizing final products at present. This method usually applies in injections to prepare labeled pharmaceuticals in advance for offering hospital use. But if quality of labeled pharmaceuticals after autoclave sterilization has been worse than the before autoclave sterilization one, autoclave sterilization may fail to use in routine need.

Another sterilizing method is by 0.22 μm Membrane Filtration method which labeled products (e.g. the PET tumor imaging agent $^{18}$F-FDG) pass through a 0.22 μm Millipore membrane. This method can filtrate bacteria effectively and remain pharmaceutical activity effectively. But standards of pharmaceutical factories should comply with a negative pressure operation, providing a Class 100 (EC GMP Grade A) air environment in virtue of using in radiolabeled products. Thus, a general pharmaceutical factory can not afford such a high Class and the cost thereof.

SUMMARY

It is therefore a first aspect of the present disclosure to provide a pharmaceutical composition, including a bi-functional compound having a ASGPR specificity to form a labeled precursor without oxidants such as chloramine T, iodobead, Iodogen or the like and with extremely low toxicity. The pharmaceutical composition can thus quantify potential of liver storage ability and evaluate severity of the course of liver disease.

It is therefore a second aspect of the present disclosure to provide a liver-receptor imaging injection for the pharmaceutical composition to form a lyophilized dosage form by lyophilization at a low-temperature and sterile condition, wherein salts in the pharmaceutical composition can operatively control the ph for labeling, so unlabeled pharmaceutical pharmaceutical composition in the lyophilized dosage form can storage at room temperature for more than two years and can apply in diagnosis of liver function after labeling by radionuclides.

It is therefore a third aspect of the present disclosure to provide a dispensing method for liver-receptor imaging injection by one step. The dispensing method is easy and rapid. Meanwhile, labeled radiochemical purity may remain more than 95% for several days. Thereby, disadvantages of the reduced labeling-yield and the instability after autoclave sterilization may be improved.

Thus, the present disclosure provides a pharmaceutical composition including a radionuclide labeled precursor, the pharmaceutical composition including:

a radionuclide labeled precursor including a bi-functional compound having a structure of formula (1),

wherein, A is an alpha-amino acid or a derivative thereof, B is selected from the group consisting of lactose, galactose and derivatives thereof, and n is an integer selected from 1 to 3;

with the proviso that the bi-functional compound further includes a structure of formula (2) provided that B is lactose or a derivative thereof;

wherein D is an amino acid or a derivative thereof having a carboxylic acid group in the side chain and k is 1 or 2;

a citrate in which the constituent is about 10 to about 100 mg; and a citric acid in which the constituent is about 10 to about 100 mg.

In some embodiments, D may be asparatic acid, glutamic acid or a derivative of the said compounds. Preferably, D is asparatic acid, or glutamic acid. More preferably, D is asparatic acid. The derivatives may preferably be (Nα-(trifluoro-acetaminohexanoyl)-L-aspartic acid), but is not limited to this.

In some embodiments, A may be lysine or the derivative thereof. Preferably, lysine may be L-lysine, but is not limited to this. Preferably, the derivative may be □-benzyloxycarbo-nyl-N,N-bis(carboxymethyl)-L-lysine, but is not limited to this. For example, derivatives with a single lysine may be used as a backbone to prepare poly-galactosamine chain or a poly-lactose chain. Alpha-amion group and glycolic acid group react under reductive alkylation, so that two $CH_2COOH$ group on the N atom and a COOH and a $NH_2$ of lysine itself are capable of forming three saccharide chain and remaining a free amion group to form a precursor of liver-receptor imaging agent which is suitable for radionuclide (e.g. $^{111}$In) labeling by further bridging DTPA.

In some embodiments, citrate may be trisodium citrate. Preferably, citric acid and citrate remain a ph of about 4 in an aquatic condition. In some embodiments, pharmaceutical composition may be a lyophilized dosage form. The lyophilized dosage form can prepare by lyophilization at a low-temperature and sterile condition. Thus, the prepared pharmaceutical composition in a lyophilized dosage can storage at room temperature for more than two years. Citric acid and citrate in the pharmaceutical composition can operatively control the pH for labeling.

The present disclosure further provides a dispensing method for dispensing a liver-receptor imaging injection, wherein the pharmaceutical composition and a radionuclide can storage in a first container and a second container respectively, then adding the radionuclide in the second container into the first container to react about 10 to 30 minutes to obtain the liver-receptor imaging injection.

In some embodiments, the pharmaceutical composition may further include a suitable amount of mannitol and form a lyophilized dosage form. In some embodiments, the dispensing method preferably may react at a room temperature, and more preferably may react at room temperature for 15 minutes to obtain the liver-receptor imaging injection.

In some embodiments, the radionuclide may be In-111, but is not limited to this. Any radionuclide capable of applying in the labeled precursor can be used.

In some embodiments, the first container may be a lyophilized vial containing the pharmaceutical composition in lyophilized dosage form, but any container for storaging lyophilized kit known to one of ordinary skill in the art may be used. While the second container may be any container which can storage radionuclides known to one of ordinary skill in the art. Radiochemical purity of the liver-receptor imaging injection labeled by the method may remain more than 95% after labeling for five days.

The present disclosure also provides a liver-receptor imaging injection prepared by the foregoing method. The liver-receptor imaging injection may used in screening of residual liver function.

The details of one or more embodiments of the invention are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DETAILED DESCRIPTION

The following examples serve to illustrate certain embodiments and aspects of the present disclosure and are not to be considered as limiting the scope thereof.

Example 1

Design for New Liver Targeted Drugs

Figure 1:
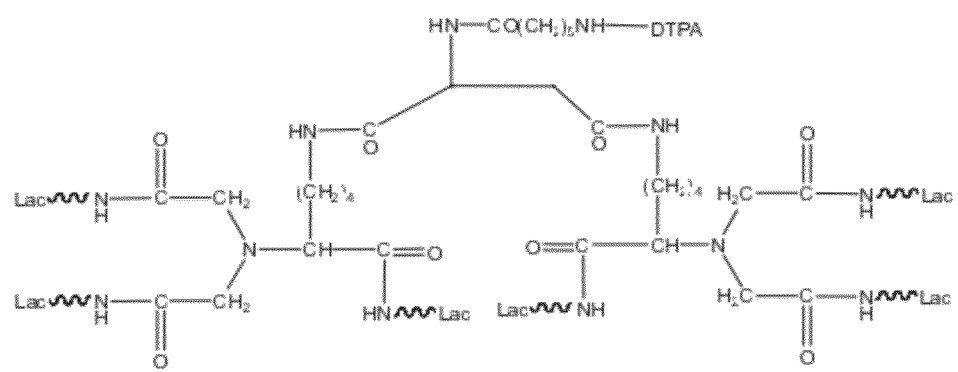
FIG. 1 illustrates a structure of the liver targeted drug in example 1.

The major pharmaceutical structure of example 1 was illustrated in FIG. 1, in which E-benzyloxycarbonyl-α-dicarboxylmethyl-L-lysine (Z-DCM-Lys) was used as a basic structure to connect aminohexyl Lac (ah-Lac) so that three-chain lactose or three-chain galactosamine (triGalNAc) formed. Because of the much cheaper price, lactose had an advantage of cost down and thus became more competitive than galactosamine or galactose.

However, binding strength of lactose chains was weaker than that of galactosamine chains, thus if binding with lactose chains, aspartic acid or glutamic acid was bound to two molecules of three-chain lactose. That is, two-molecule ε-Z-α-DCM-Lys (ah-Lac)$_3$ bound together with aminohexanoic aspartic acid (AHA-Asp) to form AHA-Asp[DCM-Lys(ah-Lac)$_3$]$_2$ (hexa-lactoside). Free amino residues of hexa-lactoside could react with DTPA anhydride in sodium carbonate solution to form DTPA derivatives of AHA-Asp[DCM-Lys(ah-Lac)$_3$]$_2$ (hereinafter called DTPA-hexa-lactoside).

Examples 2

Radiochemical Purity Before and after Autoclave Sterilization

Figure 2:
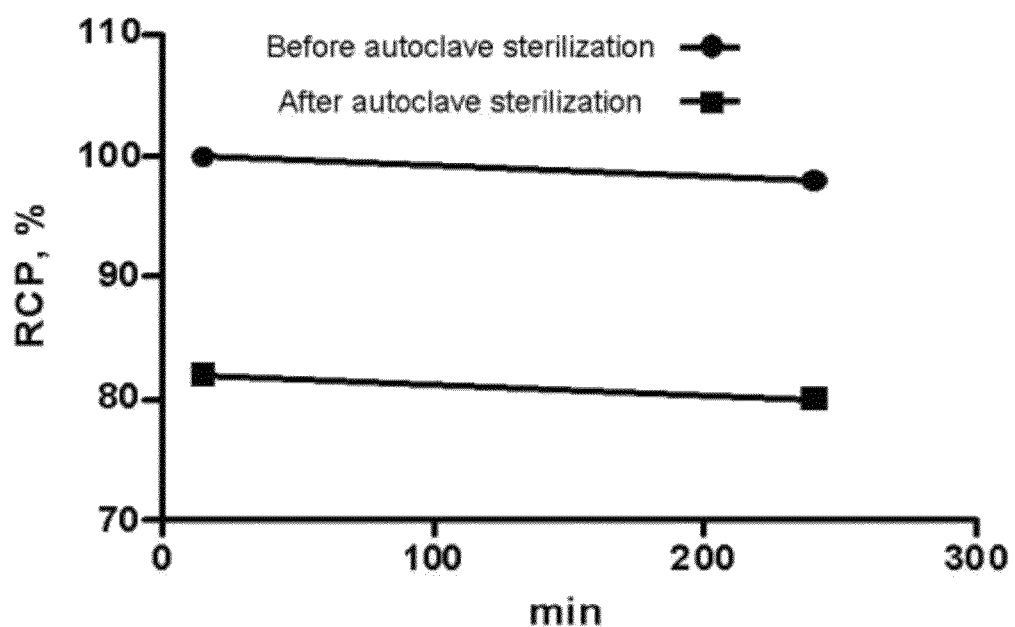
FIG. 2 illustrates the comparison of radiochemical purity between before and after autoclave sterilization.

To test whether $^{111}$In radiolabel of DTPA-hexa-lactoside was affected by autoclave sterilization, DTPA-hexa-lactoside was put into a lyophilized vial to set in an autoclave for sterilizing. After that, $^{111}$In radiolabel proceeded. The result demonstrated that radiochemical purity of $^{111}$In had an obvious decrease (<90%) after autoclave sterilization, showing that autoclave sterilization was unworkable for DTPA-hexa-lactoside. The comparison of radiochemical purity between before and after autoclave sterilization was illustrated in FIG. 2.

Example 3

Preparation of ASGPR Imaging Agents in Lyophilized Dosage Forms

Figure 3:
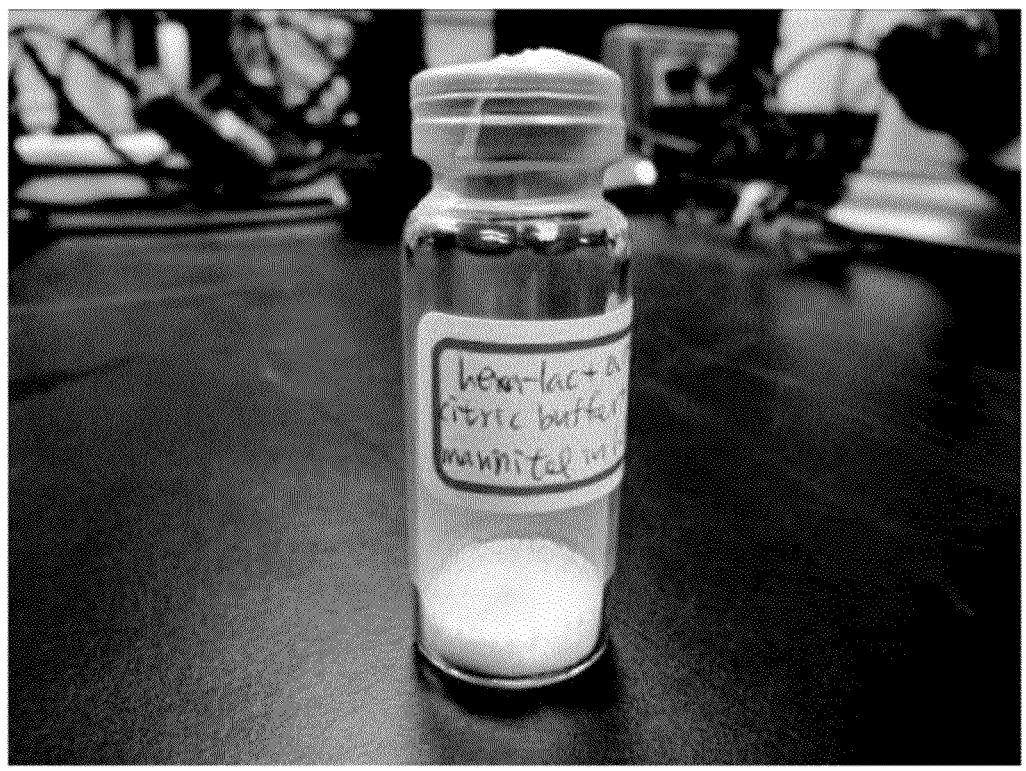
FIG. 3 illustrates the drawing of the lyophilized dosage form in example 3.

The process should operate in a sterile condition to ensure sterile quality of products. 0.08 mg DTPA-hexa lactoside, 55 mg citric acid, 62 mg trisodium citrate and 100 mg mannitol were weighed by an electronic analytical balance and poured into a 10 ml sealable react-vial. 15 ml water for injection was added into them to vortex until dissolved and nitrogen gas was incessantly introduced. The solution made from the foregoing step was filtrated with a 0.22 μm filtration film and then set separately into ten sterile and pyrogen-free vials, each of which had a volume of 10 ml. These vials were covered with an autoclaved long-legged rubber plug and pressed half of the depth to remain vent holes. These vials were rapidly moved to a freeze dryer. After drying for 18 hours, nitrogen gas was incessantly introduced and hydraulic button were controlled to press the rubber plug into the bottle mouth. After positioning the rubber plug, inlet valve of nitrogen gas were shut. These vials were taken out from the freeze dryer, sealed with red-top alumina covers one by one and storage at room temperature. The drawing of the lyophilized dosage form was shown in FIG. 3

Example 4

Radiolabeling of ASGPR Imaging Agents

Alumina covers of the foregoing vials containing ASGPR imaging agents were removed, and then these vials were put in a lead can with a suitable size. 0.5 ml indium [$^{111}$In] chloride solution (with a radioactivity of about 5 mCi) was added in these vials with a syringe, mixing for 1 to 2 minutes for fully dissolving. After the mixture stranded for 15 minutes, the sampling analysis proceeded.

Example 5

Radio-Instant Thin Layer Chromatography (Radio-ITLC) Using in to Label ASGPR Imaging Agents First, a developing solvent of radio-ITLC of 10 mM sodium citrate buffer (about pH 5) were prepared as follows: 0.13 g citric acid monohydrate and 0.11 g trisodium citrate dehydrate were weighed precisely to dissolve in 100 ml water for injection. Then 10 ml of the solution were added in the developing tank as a developing solvent. The position away from the bottom of a TLC-SG film about 2 cm was marked with a pencil as the origin while the position away from the bottom about 9 cm was marked as the end. A few samples were taken by a micropipette to drop at the origin. Then, the TLC-SG film was put in a developing tank containing a buffer (about pH 5) of 10 mM sodium citrate to develop. The film were taken out to dry in the fume cabinet while the liquid level reached the end. The film was scanned with a Radio-TLC scanner to collect the map for 1 minute and draw an integral graph.

The calculating formula is as follows:

Radiochemical purity (%)=$A/B$×100%, wherein

A refers to a calculated area peak of $^{111}$In-DTPA-hexa-lactoside (Rf=0.0-0.1), and B refers to calculated area of all peaks.

Figure 4:
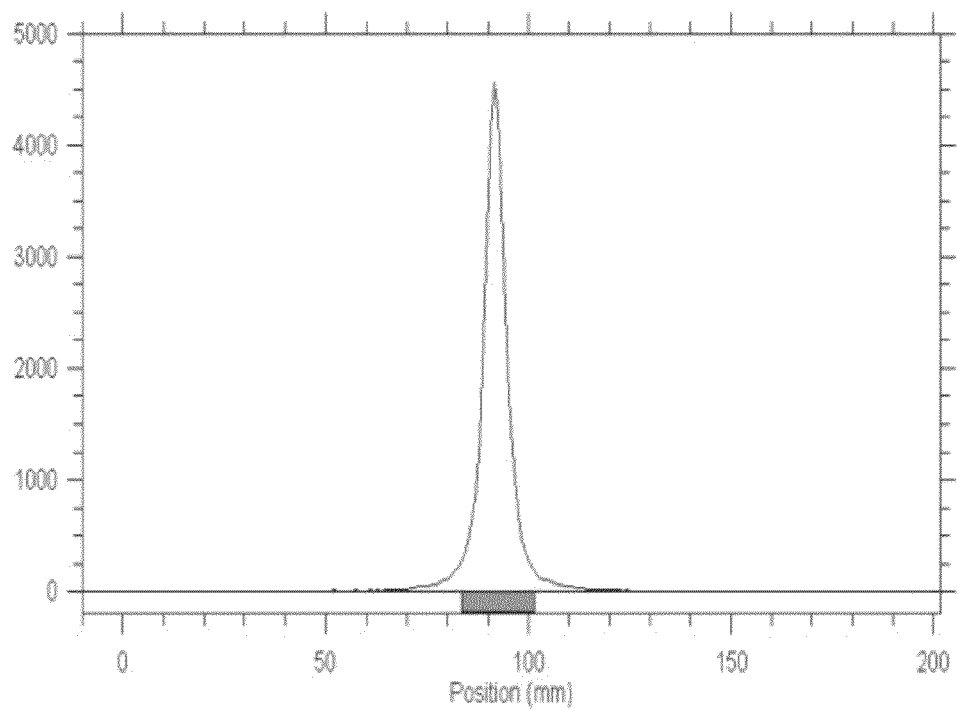
FIG. 4 illustrates TLC map of 100% 111In in example 4.
Figure 5:
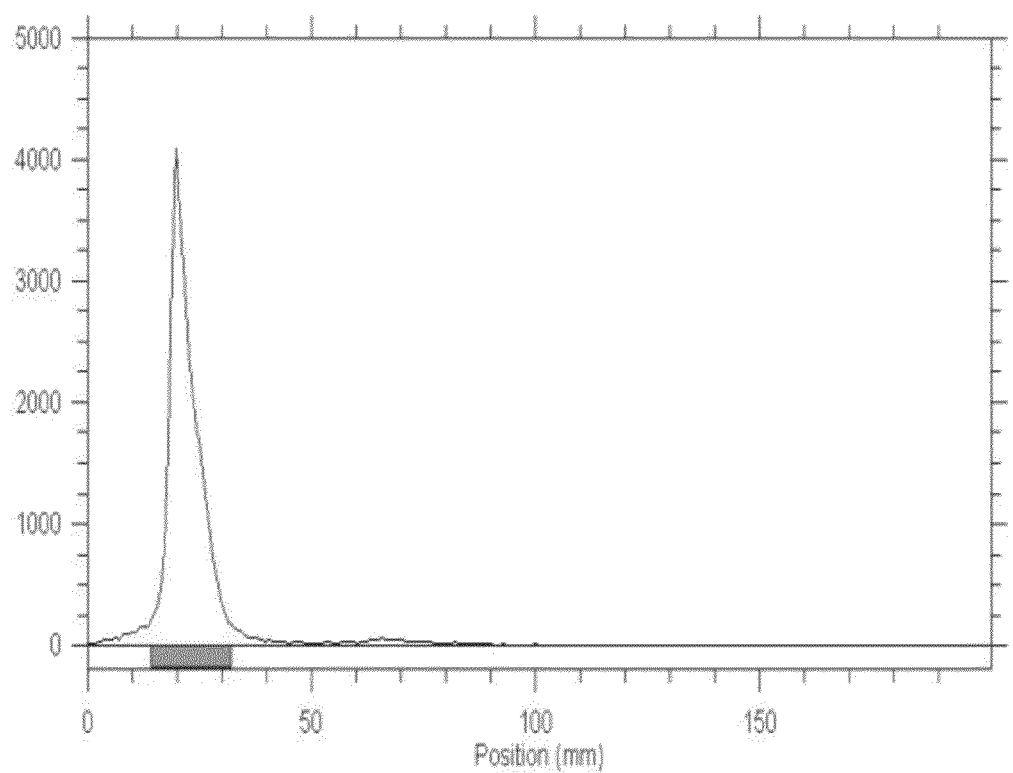
FIG. 5 illustrates TLC map of 100% 111In DTPA hexa-lactoside in example 5.

TLC map of 100% $^{111}$In was illustrated in FIG. 4, while TLC map of 100% $^{111}$In-hexa-lactoside was illustrated in FIG. 5.

Example 6

Time-Dependent Stability Test of $^{111}$In Labeled ASGPR Imaging Agents

Figure 6:
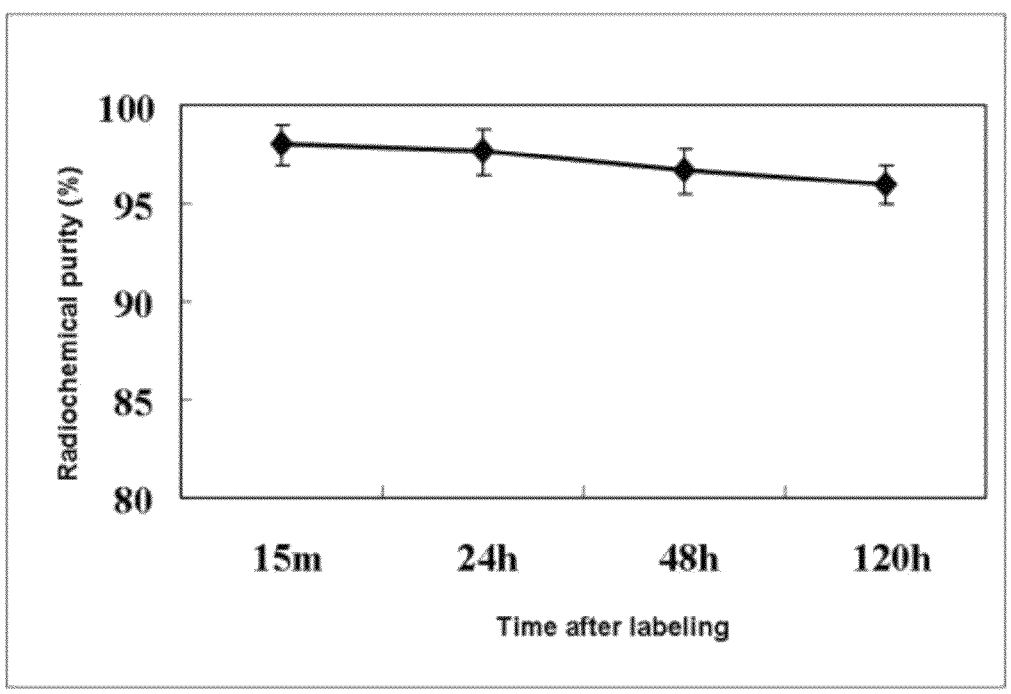
FIG. 6 illustrates the result of radiochemical purity for time-dependent stability test in example 6.

Three vials containing ASGPR imaging agents were taken for $^{111}$In labeling. reacted vials were set at room temperature to sample for analyzing radiochemical purity of radio-ITLC after labeling for 15 minutes, 24 hours, 48 hours and 120 hours, respectively. The result exhibited that radiochemical purity could still remain >95% after labeling for 120 hours and proved that $^{111}$In DTPA-hexa-lactoside had a property of high stability. The result of radiochemical purity for time-dependent stability test was illustrated in FIG. 6.

Example 7

The Effect of with or without Mannitol for Labeled Stability

Figure 7:
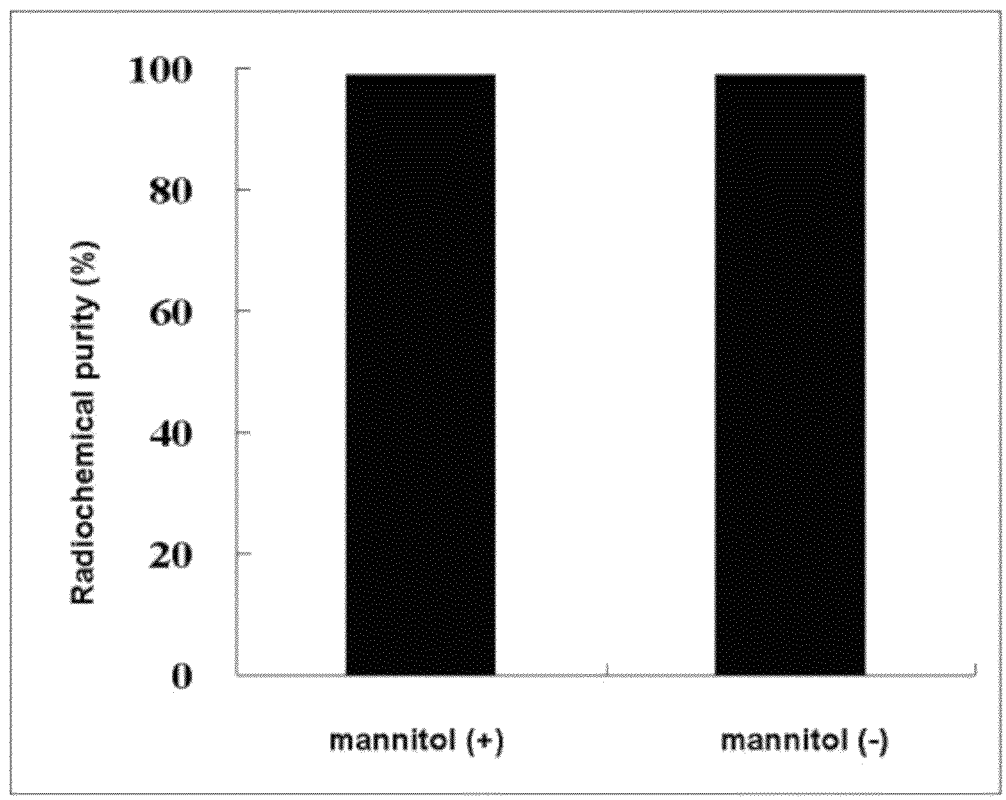
FIG. 7 illustrates the effect of with or without mannitol for labeled stability in example 7.

Two lyophilized dosage forms (a form was with mannitol and the other one was without mannitol) are respectively prepared, which the ingredients of the form with mannitol were citric acid, sodium citrate, DTPA-hexa-lactoside and mannitol while the ingredients of the form without mannitol were only citric acid, sodium citrate and DTPA-hexa-lactoside. After preparing, lyophilized dosage forms were radiolabeling with $^{111}$In for 15 minutes, and then radiochemical purity analysis proceeded by radio-ITLC. The result were shown that both lyophilized dosage forms had a radiolabeling efficiency of >95%, proven that mannitol had no effect on $^{111}$In radiolabeling efficiency of liver-receptor imaging agents. The effect of with or without mannitol for labeled stability was illustrated in FIG. 7.

Example 8

The Effect of pH for Labeled Stability

Figure 8:
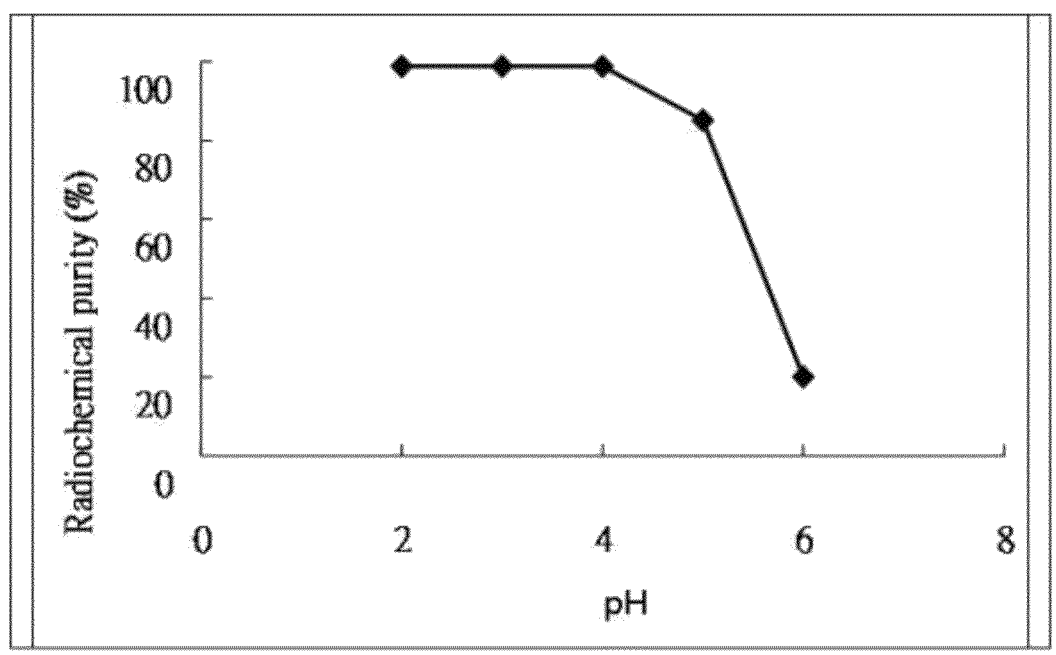
FIG. 8 illustrates the effect of pH for labeled stability in example 8.

Sodium citrate buffers of different pH were used for $^{111}$In radiolabeling of DTPA-hexa-lactoside. The result was shown that $^{111}$In radiolabeling efficiency was >95% at a pH of about 2 to 4, but $^{111}$In radiolabeling efficiency had a obvious decline at pH 6, proven that the optimal condition of $^{111}$In radiolabeling for DTPA-hexa-lactoside was the pH of about 2 to about 4. The effect of pH for labeled stability was shown in FIG. 8

Example 9

Animal Image

Figure 9:
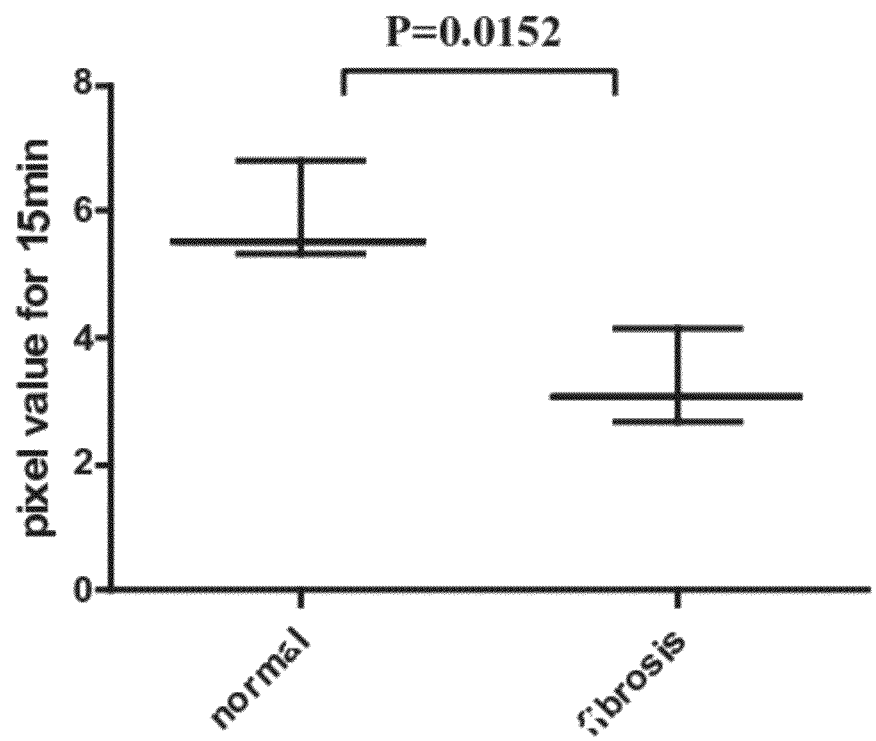
FIG. 9 illustrates the comparison of liver radioactivity for the liver fibrosis mice and the normal mice in example 9.

Each 100 μL cylinder of 1, 2, 3, 4, 5 μCi$^{111}$InCl$_3$ to make microSPECT dynamic scanning for 15 minutes, and then absorption readings were collected per minute to construct an activity-absorption curve graph. Later, $^{111}$In DTPA-hexa-Lactoside (200 nCi/g) was injected into thioacetamide-induced liver fibrosis mice from their vena caudalis. MicroSPECT image scanning proceeded, which the liver position was chosen and corresponded to the foregoing activity-absorption curve graph by interpolation, to quantitatively determine image intensity. Referring to FIG. 9, measurement of liver radioactivity for the thioacetamide-induced liver fibrosis group and the normal group was shown. The result demonstrated that liver of the thioacetamide-induced liver fibrosis group had an obviously lower absorption of $^{111}$In DTPA-hexa-Lactoside.

Above all, tests of animal and nuclear medicine application demonstrated that the liver-receptor imaging injection in the present invention may use in screening of residual liver function.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A pharmaceutical composition, wherein the pharmaceutical composition is a precursor capable of being labeled with a radionuclide for a liver receptor imaging injection, comprising:
a bi-functional compound having a structure of formula,

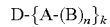

wherein A is lysine or the derivative thereof, B is lactose or a derivative thereof, D is aspartic acid or a derivative thereof, n is 1, and k is 1;
a citrate of about 10 to about 100 mg; and
a citric acid of about 10 to about 100 mg.

2. The pharmaceutical composition of claim 1, wherein the derivative of D is Nα-(trifluoroacetaminohexanoyl)-L-aspartic acid.

3. The pharmaceutical composition of claim 1, wherein the derivative of A is ε-benzyloxycarbonyl-N,N-bis(carboxymethyl)-L-lysine.

4. The pharmaceutical composition of claim 1, wherein the citrate is trisodium citrate.

5. The pharmaceutical composition of claim 1, wherein the citric acid and the citrate remain at pH of about 4 in an aquatic condition.

6. The pharmaceutical composition of claim 1, wherein the pharmaceutical composition further comprises mannitol and is a lyophilized dosage form.

7. The pharmaceutical composition of claim 1, wherein the pharmaceutical composition is a lyophilized dosage form.

8. A method for preparing a liver-receptor imaging injection, comprising steps of:
storing the pharmaceutical composition of claim 1 and a radionuclide in a first container and a second container respectively; and
adding the radionuclide in the second container into the first container to react about 10 to 30 minutes to obtain the liver-receptor imaging injection.

9. The method of claim 8, wherein the pharmaceutical composition further comprises mannitol and is a lyophilized dosage form.

10. The method of claim 8, wherein the radionuclide in the second container is added into the first container to react about 10 to 30 minutes at room temperature.

11. The method of claim 8, wherein the radionuclide is DTPA-chelated In-111.

* * * * *